(12) United States Patent
Shin et al.

(10) Patent No.: US 9,983,220 B2
(45) Date of Patent: May 29, 2018

(54) APPARATUS AND METHOD FOR PLATELET FUNCTION AND DRUG RESPONSE TESTING BASED ON MICROFLUIDIC CHIP

(71) Applicant: Korea University Research and Business Foundation, Seoul (KR)

(72) Inventors: Se Hyun Shin, Seoul (KR); Chae Seung Lim, Anyang-si (KR)

(73) Assignee: KOREA UNIVERSITY RESEARCH AND BUSINESS FOUNDATION, Seoul (KR)

(*) Notice: Subject to any disclaimer, the term of this patent is extended or adjusted under 35 U.S.C. 154(b) by 206 days.

(21) Appl. No.: 14/655,437

(22) PCT Filed: Dec. 26, 2013

(86) PCT No.: PCT/KR2013/012223
§ 371 (c)(1),
(2) Date: Jun. 25, 2015

(87) PCT Pub. No.: WO2014/104761
PCT Pub. Date: Jul. 3, 2014

(65) Prior Publication Data
US 2015/0338424 A1 Nov. 26, 2015

(30) Foreign Application Priority Data
Dec. 27, 2012 (KR) .................... 10-2012-0154057

(51) Int. Cl.
*G01N 33/86* (2006.01)
*G01N 33/49* (2006.01)
(Continued)

(52) U.S. Cl.
CPC .......... *G01N 33/86* (2013.01); *B01L 3/50273* (2013.01); *G01N 15/0612* (2013.01);
(Continued)

(58) Field of Classification Search
CPC ......... B01L 2200/10; B01L 2300/0627; B01L 2300/0645; B01L 2300/0654;
(Continued)

(56) References Cited

U.S. PATENT DOCUMENTS 5,380,491 A * 1/1995 Carver, Jr. .......... G01N 35/1095
422/73
2008/0297169 A1* 12/2008 Greenquist ....... B01L 3/502715
324/600

(Continued)

FOREIGN PATENT DOCUMENTS

| JP | 2007-521478 A | 8/2007 |
| KR | 10-2011-0088746 A | 8/2011 |
| KR | 10-1193566 B1 | 10/2012 |

*Primary Examiner* — Jennifer Wecker
(74) *Attorney, Agent, or Firm* — NSIP Law

(57) ABSTRACT

The present invention relates to an apparatus and a method for testing a function and a drug response of a platelet based on a microfluidic chip. The apparatus for test comprises a measuring device containing a blood sample and measuring aggregation and adhesion of a platelet generated by flow of the blood sample; and a fluid driving device which is connected to the measuring device and generates a oscillating shear flow of the blood sample. Therefore, activation of factors such as a platelet and von Willebrand factor (vWF) etc. can be activated uniformly and completely, and a repeatability of the platelet aggregation can be increased.

16 Claims, 8 Drawing Sheets

(51) Int. Cl.
*G01N 15/14* (2006.01)
*B01L 3/00* (2006.01)
*G01N 15/06* (2006.01)
*C12M 3/00* (2006.01)
*G01N 15/00* (2006.01)

(52) U.S. Cl.
CPC ..... *G01N 15/1463* (2013.01); *G01N 15/1484* (2013.01); *G01N 33/49* (2013.01); *B01L 3/502715* (2013.01); *B01L 2200/10* (2013.01); *B01L 2300/0627* (2013.01); *B01L 2300/0645* (2013.01); *B01L 2300/0654* (2013.01); *B01L 2300/0663* (2013.01); *B01L 2400/0406* (2013.01); *B01L 2400/0478* (2013.01); *B01L 2400/06* (2013.01); *G01N 2015/0092* (2013.01)

(58) Field of Classification Search
CPC ..... B01L 2300/0663; B01L 2400/0478; B01L 2400/06; B01L 3/50273; G01N 15/0612; G01N 15/1463; G01N 15/1484; G01N 2015/0092

See application file for complete search history.

(56) References Cited

U.S. PATENT DOCUMENTS

| | | | |
|---|---|---|---|
| 2009/0136982 A1* | 5/2009 | Tang | B01F 5/102 435/29 |
| 2010/0099130 A1* | 4/2010 | Haworth | B01L 3/502746 435/29 |
| 2012/0058500 A1* | 3/2012 | Mitchell | B01L 3/502746 435/13 |
| 2014/0315228 A1* | 10/2014 | Yuan | G01N 33/4905 435/13 |

* cited by examiner

APPARATUS AND METHOD FOR PLATELET FUNCTION AND DRUG RESPONSE TESTING BASED ON MICROFLUIDIC CHIP

CROSS-REFERENCE TO RELATED APPLICATIONS

This application is a U.S. National Stage Application of International Application No. PCT/KR2013/012223, filed on Dec. 26, 2013, which claims the benefit under 35 USC 119(a) and 365(b) of Korean Patent Application No. 10-2012-0154057, filed on Dec. 27, 2012, in the Korean Intellectual Property Office.

TECHNICAL FIELD

The invention relates to an apparatus and a method for testing a function and testing a function and a drug response of a platelet based on a microfluidic chip such that various test can be carried out automatically with a small amount of blood through the flow in a disposable microchip for early diagnosis of thrombotic ischemia and bleeders' disease.

BACKGROUND ART

Thrombosis is the formation of a hemostasis or a blood clot inside a blood vessel. Thrombosis in coronary artery of the heart or cerebrovascular part causes a heart attack or cerebral infarction. Thrombosis referred to as silent killer is becoming the main cause of death for our contemporaries. The problem is that thrombosis or bleeding disease is not caused by genetic defect only and cause thereof is not discovered clearly.

More seriously, thrombosis prevalence rate is fast increasing due to genetic defect and acquired factors. Therefore, an apparatus and method have been required to make a quantitative test for thrombosis or bleeding disease and to carry out an early diagnosis and prognosis decision.

There are many factors which play roles in hemostasis at vascular injury sites. All of biochemical and biological mechanism of each factor play a critical role and hemostasis of a platelet plays the most crucial role. A platelet is not attached to the arterial walls at no injury sites, but biochemical and biological mechanism is activated at vascular injury sites, thereby hemostasis is achieved regardless of flow conditions.

Many method and devices have been developed to subdivide and test a platelet function. A platelet function test is an important test to discern bleeding disorders which are caused by a congenital or acquired disorder of platelet function in case of the bleeding disorders having no numerical platelet disorder. Also, this platelet function test is being used to examine an increase of hemorrhage tendency or a drug-tolerance which is caused by antiplatelet agent used for the treatment or prevention of cardiovascular disorders.

If there is an injury at endothelial cells in the blood vessel, an inner material in the endothelial cells such as collagen is exposed to the blood and a platelet is attached to the material and is activated. Attachment mechanism of platelet has different characteristics depending on blood flow conditions.

In particular, if a blood flow rate is high in the artery and a shear stress applied to the blood vessel wall is high, platelet is not attached to the inner membrane of the blood vessel easily. In this condition, von Willebrand factor (vWF) is activated and is easily attached to the wall of the blood vessel and a platelet is attached to the wall of the blood vessel by vWF. Of course, it is known that a glycoproteic receptor complex such as GPIb-IX-V which is contained in the platelet cell membrane induces the reaction with vWF, leading to the attachment.

As such, an attached platelet induces an aggregation by attracting the same kind of platelet and leads to hemostasis. Then, hemostasis is reinforced by fibrin.

However, the function of platelet is not always favorable, but can produce adverse effect in a certain flow condition or situation. For example, when the blood vessel wall became narrow locally by artery hardening, a platelet passing through this narrow part is exposed to a high shear ratio and is activated, and then adhesion and aggregation occurs in the rear of the narrow part and leads to thrombosis which blocks the blood vessel.

As explained above, a platelet and vWF are activated by the size of a blood flow, i.e., a shear stress due to the flow, thereby leading to the increase of an adhesive property and the generation of hemostasis. It is known that the shear stress required for the activation of a platelet or vWF is at least 8 Pa and the shear rate is at least 5,000 l/s.

As such, various devices are suggested and developed for an early diagnosis and prognosis test of hemostasis or bleeding disease and they can be divided into an electric method, an optical method, a time measuring method to stop bleeding, etc., based on the measuring sensor.

A bleeding time (BT) method was developed about 100 years ago which measures a bleeding time and is still being used for a screening test of a platelet function. However, a current platelet function test has problems such as a difficult standardization, a low diagnostic validity and a use of invasive technique and therefore an objectified measuring method to measure a platelet function has been required.

To solve the problems, a platelet function analyzer (e.g.: PFA-100) is developed which is being used to measure a platelet function. This analyzer uses a feature that a platelet is aggregated by activated vWF in a high shear rate. To measure this feature, after whole blood flows in a long capillary tube, a platelet aggregates in an orifice coated by ADP or epinephrine together with collagen and then time by which the orifice is blocked is measure by pressure, flow rate, etc.

This platelet function test strictly depends on the function of vWF. This test has disadvantages that the test depends on hematocrit (Hct) and an antiplatelet test such as a test using aspirin or clopidogrel is not possible. Also, disadvantageously, two step tests are required for the function test of platelet and cost for the test is increasing.

In particular, to activate vWF, a blood sample must be exposed for a predetermined time with a high shear rate. For this, PFA-100 uses a method for making blood flow at high speed in a long capillary tube. However, disadvantageously, this method requires a large quantity of blood. Also, it is a disadvantage that vWF is not activated at the center of the capillary tube where a shear rate is minimum while vWF is activated near the tube wall where a shear rate is maximum, thereby a repeatability of test results is not guaranteed.

IMPACT of Diamed Co., Ltd. uses a rotation-type Couette flow in the form of Cone-Plate. In this method, a uniform shear stress is applied to the blood contained therein and an attachment degree of platelet is measured when a high shear stress is applied. Like PFA-100, this method has a disadvantage that it depends too much on the concentration and function of fibrinogen and vWF.

Verify-NOW (Accumetrics) uses a method to measure an aggregation degree of platelet by a turbidity using an optical sensor. In this method, an agonist is mixed with blood and then a microbead on which collagen is coated is reacted so that a platelet in the blood is aggregated. Then, turbidity is measured over time. The frequency of use this method is being increased recently, but this method still has disadvantages of prior methods to measure a turbidity.

DISCLOSURE OF THE INVENTION

Technical Problem

An object of the present invention is to solve the above problems and the present invention provides an apparatus and method for testing multifunction and drug-response of a platelet based on a microfluidic chip by which it is possible to make a multiple test including early diagnosis and prognosis of bleeding disease and thrombosis with a single test, thereby saving test costs and increasing a repeatability and an accuracy of test.

Another object of the invention is to provide an apparatus and method for testing multifunction and drug-response of a platelet based on a microfluidic chip by which a closure time of a blood flow can be measured automatically.

The object of the present invention will not be restricted to the above mentioned objects. A person having ordinary skill in the art to which the invention pertains can clearly understand another object which is not mentioned from an explanation below.

Technical Solution

To achieve the above object, the invention provides an apparatus for testing a function and a drug response of a platelet based on a microfluidic chip comprising: a measuring device containing a blood sample and measuring aggregation and adhesion of a platelet generated by flow of the blood sample; and a fluid driving device which is connected to the measuring device and generates a oscillating shear flow of the blood sample.

The measuring device comprises: a sample container containing the blood sample therein; a micro channel connected to the sample container and guiding the shear flow of the blood sample; a measuring chamber connected to the micro channel, wherein the aggregation and the adhesion of the platelet is generated in the measuring chamber; and a sensing part measuring the aggregation and the adhesion of the platelet generated in the measuring chamber.

Further, the fluid driving device comprises: a linear actuator; a piston linearly reciprocating which is driven by the linear actuator; and a cylinder in which the piston is installed such that the piston linearly reciprocates therein.

Further, a valve is installed between the measuring device and the fluid driving device and controls supply and cut-off of a driving pressure.

Further, the valve may generate a pulsatile flow through periodic open and close.

Further, the plurality of the micro channel is arranged in parallel.

Further, reagents which are different from each other are supplied in the measuring chamber connected to the micro channel arranged in parallel.

Further, the sensing part comprises at least one of an electrode sensor measuring electrical impedance, an optical sensor measuring turbidity, a pressure sensor measuring a fluctuation pressure, and an image sensor measuring a oscillating flow distance of the blood sample.

Further, the electrode sensor has two electrodes which are installed at both side in the measuring chamber and measures the change of the electrical impedance which is changed by the aggregation and adhesion of the platelet in the measuring chamber.

Further, the optical sensor is disposed opposite to a light source outside of the measuring chamber and measure the change of the optical turbidity which is changed by the aggregation and adhesion of the platelet in the measuring chamber.

Further, the pressure sensor is disposed at the valve connecting the measuring device with the fluid driving device or in the sample container, and measures the change of the fluctuation pressure which is changed by the aggregation and adhesion of the platelet in the measuring chamber.

Further, the image sensor comprises: a light source; and an optical measuring sensor receiving a light which transmits through the blood sample in the micro channel and converting the received light to an electrical signal, such that measuring the oscillating flow distance of the blood sample.

Further, the light source comprises a light emitting diode (LED), and wherein the optical measuring sensor comprises a charge coupled device (CCE) sensor array.

Further, the measuring chamber is positioned at the central part of the micro channel, and a rapidly channel-expanding part is formed in the measuring chamber and decreases a flow velocity of the blood sample.

Further, a plurality of micro-pillars is installed in the measuring chamber and induces the decrease of the flow of the blood sample by promoting the aggregation and the adhesion of the platelet.

Further, the measuring chamber is equipped with a plurality of beads therein.

Further, or more type of the reagents which is selected among Fibrinogen, Arachidonic acid, Collagen, Epinephrine, Adenosine diphosphate (ADP), Prostaglandin E1 (PGE1), Thrombin receptor activating peptide (TRAP), P2Y1 receptor antagonist, and P2Y12 receptor antagonist supplied in the measuring chamber.

Further, the P2Y1 receptor antagonist comprises one of more type of the drug which is selected among MRS 2179, MRS 2279, MRS 2500, A2P5P, A3P5P, and A3P5PS.

Further, the P2Y12 receptor antagonist comprises one or more type of the drug which is selected among Clopidogrel, Ticlopidine, Prasugrel, AR-C67085MX, Cangrelor, C1330-7, MRS 2395, and 2-methylthioadenosine-5'-monophosphate.

Further, the drug is supplied through at least one method of a surface coating and a liquid injection.

A minimum shear rate in the shear flow generated by the fluid driving device is at least 5000 $s^{-1}$; and a minimum shear stress in the shear flow generated by the fluid driving device is at least 8 Pa.

Also, the invention provided a method for a platelet function and drug response test based on a microfluidic chip comprising: injecting a blood sample into sample containers which are disposed both sides; generating a oscillating shear flow of the blood sample through a micro channel connected to the sample container; supplying a drug in a measuring chamber which is positioned at the central part of the micro channel, the drug reacts the platelet; and measuring a change which is caused by an aggregation and adhesion of a platelet in the measuring chamber.

Advantageous Effect

According to the above features, it is possible to test a blood sample through parallel channels using reagents which are different from each other. Also, with a single test only, it is possible to make a multiple test regarding a complex platelet function by performing a multiple drug tests for a single blood sample in a plurality of channels, thereby saving time and cost for a test.

Also, the blood sample can be exposed to a shear oscillating flow more than critical shear stress for enough time in each channel, such that activation of factors such as a platelet and von Willebrand factor (vWF) etc. can be activated uniformly and completely in comparison to once-through flow and a repeatability of the platelet aggregation can be increased.

Further, an adhesion and aggregation state of the platelet can be observed through a microscope in real time. Therefore, it is possible to analyze quantitatively by drug.

Further, elements which will be in contact with blood can be made of disposable and be discarded after use. Therefore, it is easy to use and avoid a blood-borne infection.

Further, it is easy to make a bulk test by means of a system having a short measuring time and enabling a simultaneous test on various samples.

Further, various agonist and antagonist can be injected directly by liquid state or can be coated on a predetermined surface of a flow path. Therefore, it is possible to carry out various pharmacologic tests.

BRIEF DESCRIPTION OF THE DRAWINGS

FIG. 5b is a graph which is measured by the sensing part in FIG. 5a.

FIG. 6b is a graph which is measured by the sensing part in FIG. 6a.

FIG. 7b is a graph which is measured by the sensing part in FIG. 7a.

FIGS. 8b and 8c are graphs which are measured by the sensing part in FIG. 8a.

MODE FOR CARRYING OUT THE INVENTION

Hereinafter, an apparatus and method for a platelet function and drug response test based on a microfluidic chip according to one embodiment of the present invention will be explained in detail referring to attached drawings.

Figure 1:
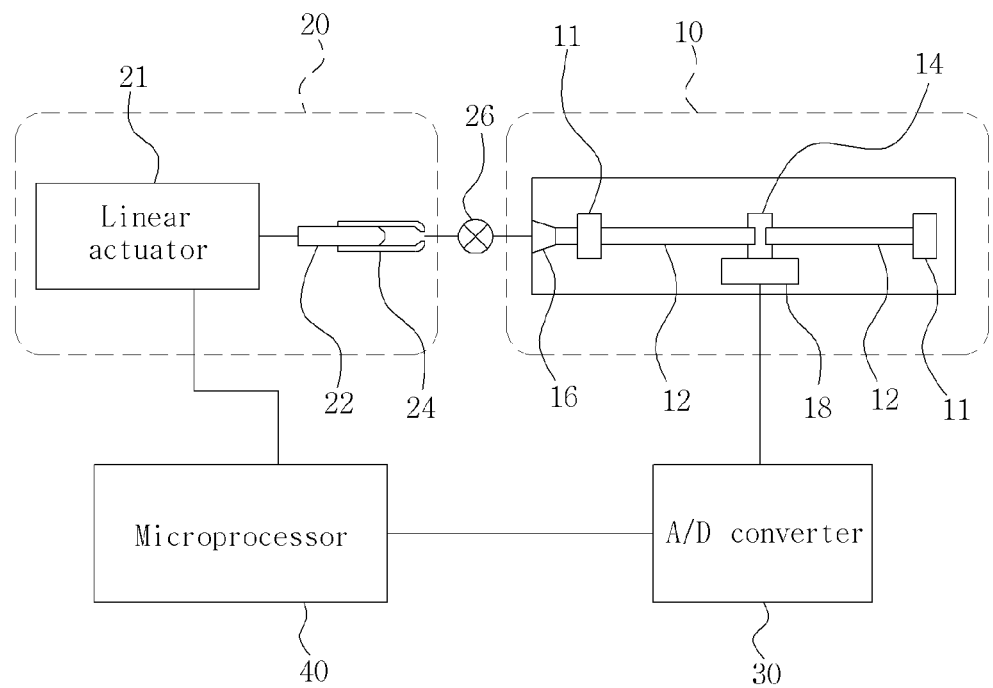
FIG. 1 shows an apparatus and method for a platelet function and drug response test based on a microfluidic chip according to one embodiment of the present invention.
Figure 2A:
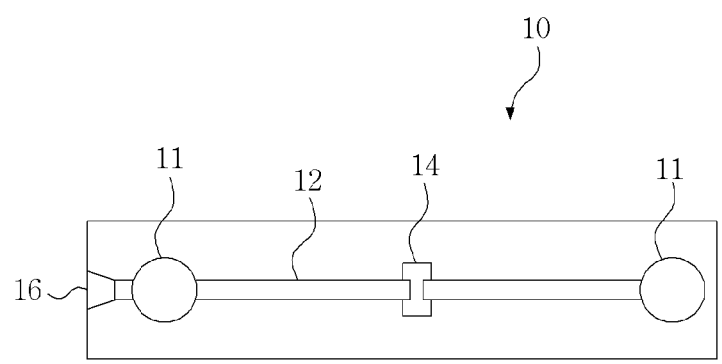
FIGS. 2a and 2b show a measuring device according to one embodiment of the present invention.
Figure 2B:
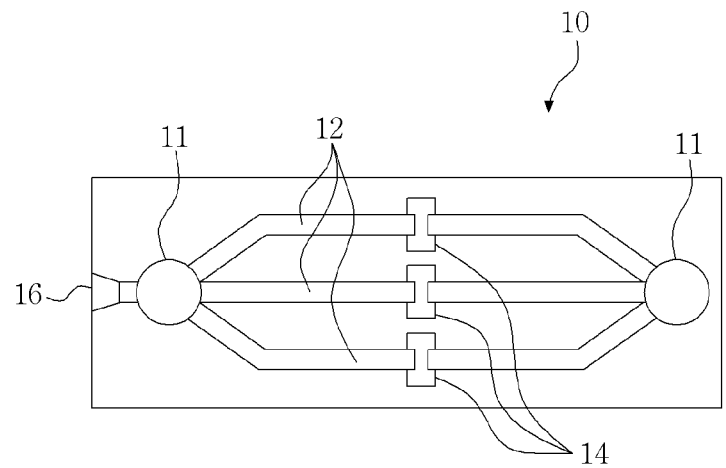

FIG. 1 shows structure of the apparatus for testing the function and the drug response of the platelet based on the microfluidic chip according to one embodiment, and FIGS. 2a and 2b show structure of a measuring device according to one embodiment of the present invention.

As shown in FIGS. 1, 2a, and 2b, the apparatus for testing the function and the drug response of the platelet based on the microfluidic chip according to the present invention comprises the measuring device 10 containing a blood sample and measuring an aggregation and adhesion of the platelet generated by flow of the blood sample; and a fluid driving device 20 which is connected to the measuring device and generates an oscillating shear flow of the blood sample.

The measuring device 10 comprises a sample container 11 which contains the blood sample therein. Also a micro channel 12 is connected to one side of the sample container 11. The micro channel 12 is connected for guiding a shear flow of the blood sample, and is connected between the sample soring chambers 11.

The micro channel 12 may have a polygonal shape such as quadrilateral, a circular shape, or an elliptical shape as cross sectional shape. For example, in case of having a square shape as the cross sectional shape, a length of one side may be 1 μm to 1000 μm, preferably 10 μm to 20 μm, more preferably 20 μm to 50 μm. In case of having the circular shape as the cross sectional shape, a diameter may be the range described above.

The micro channel 12 may comprise one channel as shown in FIG. 2a, or comprise a plurality of channels which are arranged in parallel as shown in FIG. 2b. When the micro channels 12 are arranged in parallel, reagents of different type may be supplied in each measuring chambers 14.

Also, the measuring chamber 14 for measuring an aggregation and adhesion of a platelet is connected to one side of the micro channel 12. The measuring chamber 14 is preferably positioned at the central part of micro channel 12 where the aggregation and adhesion of a platelet is appeared. Herein, a sealing part 16 for sealing may be installed at the end of the micro channel 12.

Figure 3:
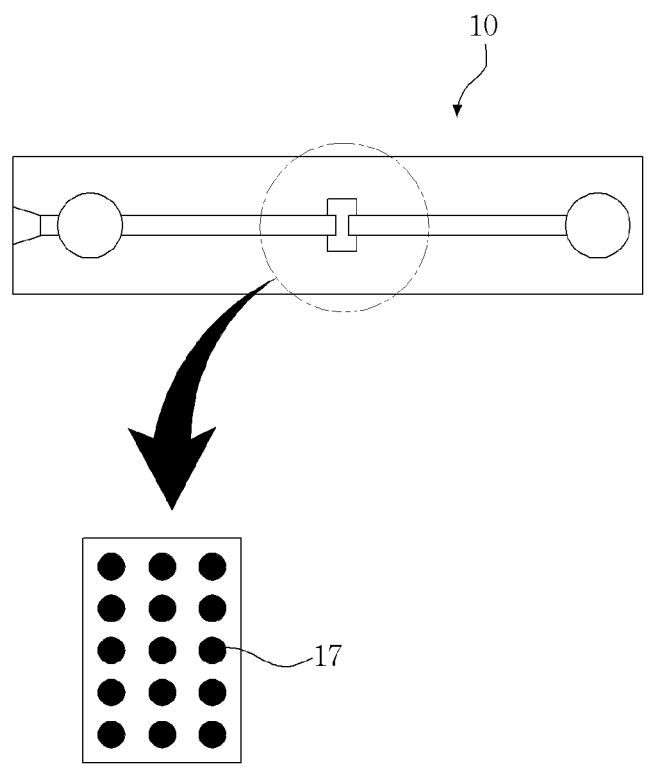
FIG. 3 shows micro-pillars which is disposed in a measuring chamber.
Figure 4:
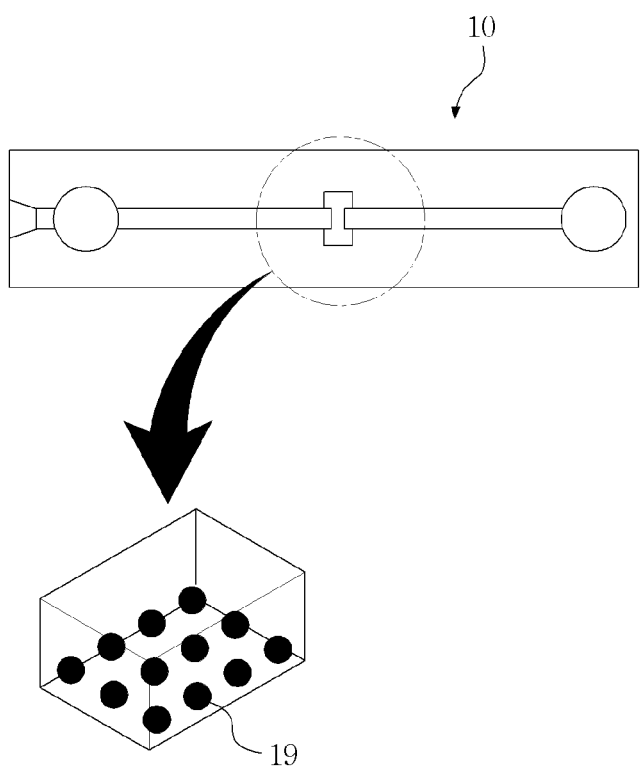
FIG. 4 shows beads which is disposed in the measuring chamber.

Referring to FIGS. 3 and 4, a plurality of micro-pillars 17 may be installed in the measuring chamber 14 and induce the decrease of the flow of the blood sample by promoting the aggregation and the adhesion of the platelet. Ultimately, the micro-pillars 17 ultimately easily stop with the channel for the oscillating flow of the blood sample. Also, the measuring chamber 14 is equipped with a plurality of beads 19 therein.

Also, a rapidly channel-expanding part (not shown) may be formed in the measuring chamber, and may decrease a flow velocity of the blood sample.

A drug may be supplied in the measuring chamber 14. The drug may be a single drug or combination of two or more reagents which is selected among Fibrinogen, Arachidonic acid, Collagen, Epinephrine, Adenosine diphosphate (ADP), Prostaglandin E1 (PGE1), Thrombin receptor activating peptide (TRAP), P2Y1 receptor antagonist, and P2Y12 receptor antagonist.

For example, the combination of Fibrinogen and Arachidonic acid, the combination of Collagen and Epinephrine, the combination of Collagen and Adenosine diphosphate (ADP), the combination of Collagen and Arachidonic acid, the combination of Collagen, Adenosine diphosphate (ADP) and Prostaglandin E1 (PGE1) (or P2Y12 assay), the combination of Collagen and MRS 2179, the combination of Collagen and MRS 2395, the combination of Collagen and TRAP, the combination of Collagen and P2Y1 antagonist, or the combination of Collagen and P2Y12 antagonist can be available as the combination of the reagents.

Also, one of Aspirin, P2Y1 antagonist clopidogrel, and Ticlopidine may be supplied in the measuring chamber 14 as an anti-aggregating reagent.

Meanwhile, a method for supplying the drug which is supplied in the measuring chamber 14 may comprise one of a method for coating the drug on the surface of the measuring chamber 14, a method for adding the micro-pillars 17 and/or the beads 19 which is coated with the drug in the measuring chamber 14, and a method for injecting the drug which has the liquid state in the measuring chamber 14. Also, combination of two or more methods among the above mentioned method may be applied as the method for supplying the drug.

Next, a sensing part 18 which measures the aggregation and the adhesion of the platelet by using various kinds of sensors is disposed at the measuring chamber 14. At least one of an electrode sensor measuring electrical impedance, an optical sensor measuring turbidity, a pressure sensor measuring a fluctuation pressure, and an image sensor measuring an oscillating flow distance of the blood sample may be used as the sensing part 18. Also, the sensing part 18 is connected to an A/D convertor 30 so that the measured signal can be converted.

Hereinafter, the fluid driving device 20 is explained referring to FIG. 1 before the detailed embodiments of the sensing part 18 are explained.

The fluid driving device 20 generates a linearly reciprocating motion of the blood sample which flows into the micro channel 12, and comprises a linear actuator 21, a piston 22 linearly reciprocating which is driven by the linear actuator 21, and a cylinder 24 in which the piston 22 is installed such that the piston 22 linearly reciprocates therein.

Also, a valve 26 is connected between the measuring device 10 and the fluid driving device 20. The valve 26 is actually connected to the micro channel 12, and performs control of supply and cut-off of a driving pressure. Also, valve 26 may generate a pulsatile flow through open and close for effective transmission of the driving pressure.

The flow which is generated in the micro channel 12 is designed for providing above a critical shear stress and/or a critical shear rate which is enough to dynamically stimulate and activate elements such as the platelet, von Willebrand factor (vWF), etc. in the blood sample. Here, it is preferable that a minimum shear stress is 8 Pa, and a minimum shear rate 5000 s$^{-1}$.

It requires that velocity of flow and the micro channel 12 are accurately designed and controlled for supplying the critical shear flow. Also, the time for the oscillating flow may be controlled accurately for supplying enough time for activating the platelet and the von Willebrand factor (vWF) through the shear flow.

Meanwhile, the linear actuator 12 is connected to a microprocessor 40 such that the microprocessor 40 controls the linear actuator 12.

Hereinafter, the various embodiments of the sensing part 18 are explained in detail referring to FIGS. 5 to 8.

First, for an electrical measuring method, two electrodes 14a, 14b are installed at both side in the measuring chamber 14 and measure the change of the electrical impedance. Here, the surface of the measuring chamber 14 may be coated with at least one of various agonist candidate materials.

If the high shear stress and the high shear rate are applied in the blood while the blood sample flows oscillately at high speed in the measuring chamber 14, the platelet and the von Willebrand factor (vWF) which are exposed to the high shear stress and the high shear rate are activated. Also, adhesiveness of the platelet and the von Willebrand factor (vWF) increases such that the platelet and the von Willebrand factor (vWF) are adhered to the inner surface of the measuring chamber 14 and are aggregated by degree.

Most of blood corpuscles are non-electric conductor, but the blood plasma is a good electric conductor which is a liquid with electrolyte. Thus, the electrical impedance is increased greatly when the platelet is adhered to the surface of the electrode 14a, 14b, but the electrical impedance is decreased when the platelet is adhered to the measuring chamber 14.

Figure 5A:
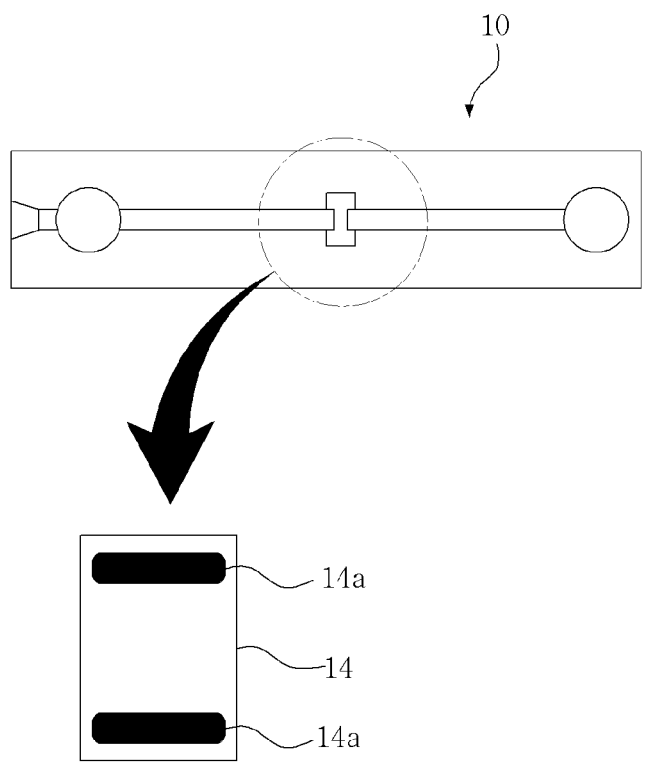
FIG. 5a shows a sensing part which measures based on electrical impedance.

Thus, it may be designed that the electrical impedance is increased or decreased according to an internal structure design of the measuring chamber 14 and a composition of the coating surface. FIG. 5a shows that an electric resistance between the electrodes 14a, 14b is increased.

Figure 5B:
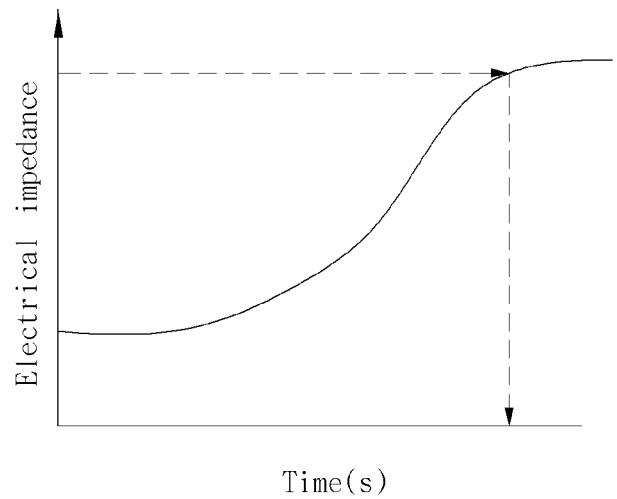

Referring to FIG. 5b, the electrical impedance asymptotically comes near a maximum value in process of time. At this time, the time of reaching 95% of a dynamic range is defined as a closure time.

Figure 6A:
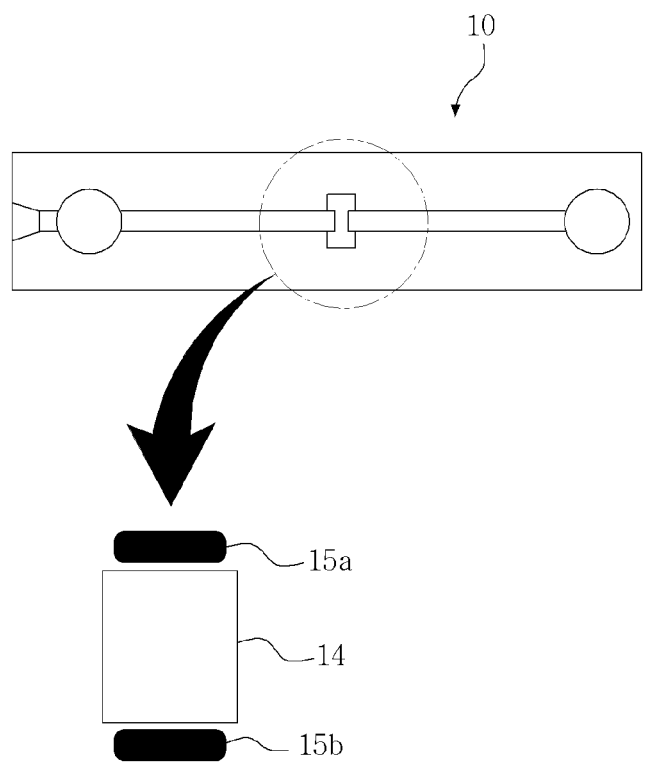
FIG. 6a shows a sensing part which measures turbidity by an optical sensor.

With regard to the other measuring method, referring to FIG. 6a, the measuring chamber 14 is made of transparent material. Also, a light source 15a and on optical sensor 15b are disposed opposite to each other outside of the measuring chamber 14, are disposed upper side and lower side of the measuring chamber 14, respectively, and measure a change of an optical turbidity in the measuring chamber 14.

The optical signal which is measured by the aggregation and the adhesion of the platelet may be increased or decreased as time passes in accordance with a structural disposition of the coating surface of the agonist between the light source 15a and the optical sensor 15b.

Figure 6B:
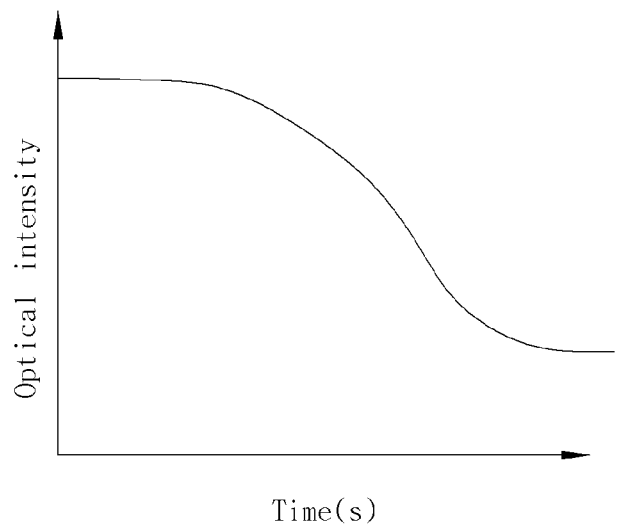

When the agonist is coated on the inner surface of the measuring chamber 14 which is inside the surface to which the light source 15a and the optical sensor 15b are disposed, the optical intensity is decreased as time passes, as shown in FIG. 6b. However, when the aggregation and the adhesion of the platelet is occurred at another portion of the surface which has minor influence on an optical path or at the micro-pillars 17, the optical intensity is increased as time passes. Also, the time of reaching 95% of the dynamic range may be determined as the closure time in common with the case of the impedance.

Figure 7A:
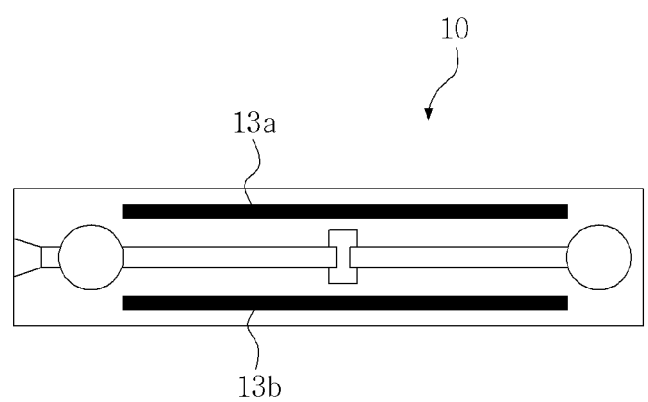
FIG. 7a shows a sensing part which measures a flow distance of the blood sample in micro channel by an image sensor.
Figure 7B:
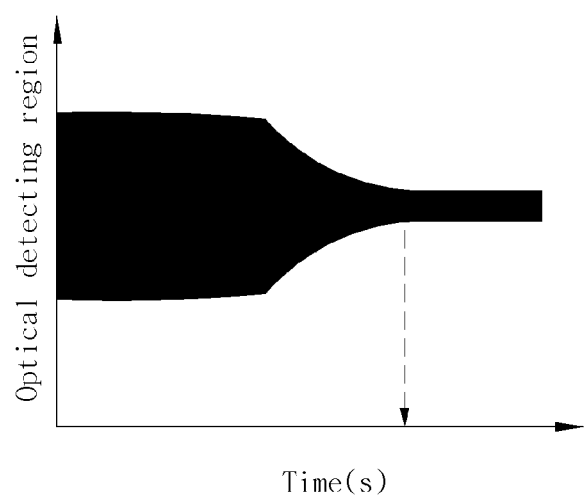

With regard to another measuring method, referring to FIG. 7a, an optical measuring sensor 13b such as a CCD sensor array etc. and a light source 13a such as LED etc. may be disposed upper side and lower side of the micro channel 12 which is connected to both side of the measuring chamber 14, respectively.

When the non-transparent blood sample flow oscillately, the measuring distance measured by the optical measuring sensor 13b is long and constant. However, the measuring distance of the blood sample is decreased in accordance with the aggregation and the adhesion of the platelet. Also, the measuring distance of the blood sample becomes the same as the distance of the micro channel 14, and becomes constant, when the measuring chamber 14 is clogged completely (Referring to FIG. 7b). Also, the time of reaching 95% of the dynamic range may be determined as the closure time in common with the case of the impedance.

Figure 8A:
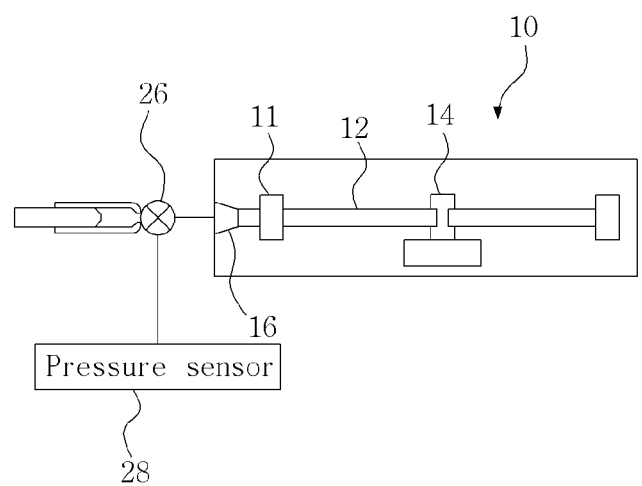
FIG. 8a shows a sensing part which measures a fluctuation pressure.

With regard to another measuring method, referring to FIG. 8a, a pressure sensor 28 may be disposed to a conduit which is connected to the other side of the valve 26 which is connected the cylinder 24.

The pressure sensor 28 is means for measuring a fluctuation pressure when the oscillating flow is applied. In the initial stages, the amplitude of the fluctuation pressure generated by the reciprocating motion of the piston 22 is slightly decreased through the oscillating flow of the blood sample. However, the original fluctuation pressure is recorded because the fluctuation pressure isn't buffered in the clogged channel when the platelet is aggregated with and is adhered to the measuring chamber 14 and the flow channel is finally clogged.

Figure 8B:
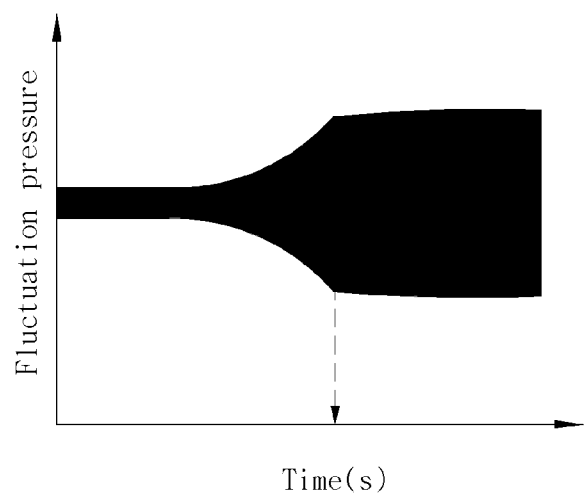

According to this embodiment, FIG. 8*b* shows a graph of the fluctuation pressure which is recorded as time passes.

Figure 8C:
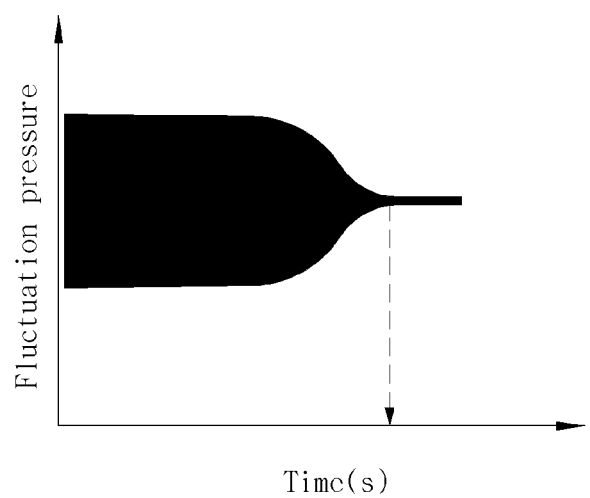

However, in case that the conduit which is connected to the pressure sensor 28 is connected to the upper part of the sample container 11 in which the blood sample is injected, and an inlet is sealed after injecting of the blood sample, the measured fluctuation pressure may be gradually decreased as time passes, as shown in FIG. 8*c*.

In the above mentioned structures, the microfluidic chip will be made of disposable, because all parts which contact the blood sample are made of plastic, glass, etc. which is quite inexpensive. As one embodiment of the present invention, the micro channel 12 may be replaced with a capillary tube for measuring a hematocrit. Also, the disposable test kit will be discarded after use. Therefore, it is easy to use and avoid a blood-borne infection.

Also, the disposable test kit may be made of a transparent material. Therefore, a mobility of the platelet can be measured by the optical measuring sensor 13*b*. Furthermore, the state of aggregation and adhesion of the platelet can be observed through a microscope.

The observation through the microscope may be used as means for research which can ordinarily observe and test a pharmacokinetic reaction against various reagents which is injected in or coated on the measuring chamber 14.

The reagents may comprise an agonist which assists the platelet in adhering, such as Collagen, Adenosine diphosphate (ADP) and Epinephrine, etc. On the other hand, the reagents may comprise an antagonist which disturbs and inhibits the aggregation of the platelet, such as Aspirin, P2Y1 receptor antagonist, and P2Y12 receptor antagonist, etc.

P2Y1 receptor antagonist may be at least one of candidate materials such as MRS 2179, MRS 2279, MRS 2500, A2P5P, A3P5P, and A3P5PS, etc. P2Y12 receptor antagonist may be at least one of candidate materials such as Clopidogrel, Ticlopidine, Prasugrel, AR-C67085MX, Cangrelor, C1330-7, MRS 2395, and 2-methylthioadenosine-5'-monophosphate, etc.

In particular, for a taker who took the above reagents, the aggregation function of the platelet and the resistance to the reagents can be measured by the test apparatus according to the invention.

For the measurement of the function of a platelet, blood from a normal person or a taker who took Aspirin and Clopidogrel is collected in citrated tubes. Then, 50 to 100 microliter of whole blood is taken and is reacted at 37° C. for 10 to 30 minutes using optimum concentration of Adenosine diphosphate (ADP), Prostaglandin E, Fibrinogen and Arachidonic acid, respectively. After the reaction, blood is migrated by applying the pressure to the microfluidic chip with micro channel 12. If the function of platelet is normal, the flow path in the measuring chamber 14 is clogged in a short time and then the flow is stopped. On the contrary, if the function of platelet is abnormal, the time for clogging will be lengthened compared to when the function of a platelet is normal.

Regarding the test of a drug tolerance, in particular when Aspirin, Clopidogrel, Ticlopidine, etc. is taken, the aggregation function of the platelet is decreased. Therefore, the flow path in the measuring chamber 14 is not clogged easily so that the clogging time is increased. Since the normal person reacts to the drug well, the clogging time is short. If the ratio of the clogging time is decreased remarkably compared to the normal person, it is determined to be the drug tolerance to Aspirin and Clopidogrel. Regarding a standard for determination, in case of Verify NOW, a predetermined cutoff OD value (550 ARU-aspirin reaction unit) for Aspirin may be determined, and then it is determined as a tolerance drug reaction if a measured value is below the standard, and it is determined as a normal drug reaction if the measured valve is above the standard. Also, in case of Clopidogrel, it is determined as an inhabitation drug tolerance if the measured value is 40% to 60% of the normal, and is determined as the tolerance if the measure value is below 20%.

The method for injecting the drug comprises the method for coating on the surface of the measuring chamber 14 as the typical method. Also, the surface of the micro-pillars 17 in the measuring chamber 14 may be coated by different kind of reagents, and the liquefied drug may be injected into the measuring chamber 14, directly. Also, the different kind of reagents may be coated on the surface of the micro channel 12.

The reagents have features of being easily mixed with the blood sample through the oscillating flow mechanism and the structure of the measuring chamber 14 according to the present invention. Therefore, various agonist and antagonist which are liquefied or solid state will be mixed with the blood, such that used as means for researching the reaction.

The scope of the present invention is not limited to the above described embodiments and is determined by the accompanying claims. It is apparent that various variations or modifications can be made within the scope of the claims by those skilled in the art.

LIST OF REFERENCE NUMERALS

10: measuring device
11: sample container
12: micro channel
13*a*: light source
13*b*: optical measuring sensor
14: measuring chamber
15*a*: light source
15*b*: optical sensor
16: sealing part
18: sensing part
20: fluid driving device
21: linear actuator
22: piston
24: cylinder
30: A/D converter
40: microprocessor

The invention claimed is:

1. An apparatus to test a function and a drug response of a platelet based on a microfluidic chip, the apparatus comprising:
a measuring device comprising sample containers containing a blood sample, a micro channel connecting the sample containers and configured to guide a shear flow of the blood sample, a measuring chamber connected to the micro channel at a center of the micro channel, and a sensor configured to measure aggregation and adhesion of a platelet generated in the measuring chamber; and
a fluid driving device connected to the measuring device and configured to generate a linearly reciprocating flow of the blood sample which is in the micro channel, wherein the aggregation and the adhesion of the platelet is generated in the measuring chamber while the blood sample reciprocately flows along the micro channel, wherein the micro channel is arranged in parallel with other micro channels, and wherein reagents which are different from each other are supplied in the measuring chamber.

2. The apparatus according to claim 1, wherein the fluid driving device comprises a linear actuator, a piston driven by the linear actuator and configured to linearly reciprocate, and a cylinder housing the piston and configured to enable the piston linearly to reciprocate in the cylinder.

3. The apparatus according to claim 1, further comprising a valve installed between the measuring device and the fluid driving device and configured to control supply and cut-off of a driving pressure.

4. The apparatus according to claim 3, wherein the valve is configured to generate a pulsatile flow through periodic opening and closing of the value.

5. The apparatus according to claim 1, wherein the sensor comprises any one or any combination of any two or more of an electrode sensor configured to measure electrical impedance, an optical sensor configured to measure turbidity, a pressure sensor configured to measure a fluctuation pressure, and an image sensor configured to measure a oscillating flow distance of the blood sample.

6. The apparatus according to claim 5, wherein the electrode sensor comprises two electrodes installed in the measuring chamber and configured to measure a change of the electrical impedance caused by the aggregation and adhesion of the platelet in the measuring chamber.

7. The apparatus according to claim 5, wherein the optical sensor is disposed opposite to a light source outside of the measuring chamber and configured to measure a change of the optical turbidity which caused by the aggregation and adhesion of the platelet in the measuring chamber.

8. The apparatus according to claim 5, wherein the pressure sensor is disposed at the valve connecting the measuring device with the fluid driving device or in the sample container, and is configured to measure a change of the fluctuation pressure caused by the aggregation and adhesion of the platelet in the measuring chamber.

9. The apparatus according to claim 5, wherein the image sensor comprises a light source, and an optical measuring sensor configured to receive a light which is transmitted through the blood sample which is in the micro channel, and convert the received light to an electrical signal to measure the oscillating flow distance of the blood sample.

10. The according to claim 9, wherein the light source comprises a light emitting diode (LED), and wherein the optical measuring sensor comprises a charge coupled device (CCD) sensor array.

11. The apparatus according to claim 1, wherein a rapidly channel-expanding part is formed in the measuring chamber to decrease a flow velocity of the blood sample.

12. The apparatus according to claim 1, wherein micropillars are installed in the measuring chamber and to induce a decrease of the flow of the blood sample by promoting the aggregation and the adhesion of the platelet.

13. The apparatus according to claim 1, wherein the measuring chamber contains.

14. The apparatus according to claim 1, wherein the reagents comprise any one or any combination of any two or more of Fibrinogen, Arachidonic acid, Collagen, Epinephrine, Adenosine diphosphate (ADP), Prostaglandin E1 (PGE1), Thrombin receptor activating peptide (TRAP), P2Y1 receptor antagonist, and P2Y12 receptor antagonist.

15. The apparatus according to claim 14, wherein the P2Y1 receptor antagonist comprises any one of any combination of any two or more of MRS 2179, MRS 2279, MRS 2500, A2P5P, A3P5P, and A3P5PS, wherein the P2Y12 receptor antagonist comprises any one or any combination of any two or more of Clopidogrel, Ticlopidine, Prasugrel, AR-C67085MX, Cangrelor, C1330-7, MRS 2395, and 2-methylthioadenosine-5'-monophosphate, and wherein the drug is supplied by either one of both of a surface coating and a liquid injection.

16. The apparatus according to claim 1, wherein a minimum shear rate of the shear flow which is generated by the fluid driving device is at least 5000 $s^{-1}$; and wherein a minimum shear stress of the shear flow which is generated by the fluid driving device is at least 8 Pa.

* * * * *